United States Patent [19]

Smith

[11] 4,140,125
[45] Feb. 20, 1979

[54] SURGICAL TAPE DEVICE

[75] Inventor: Gordon E. Smith, Sun Prairie, Wis.

[73] Assignee: Med-Pro, Ltd., Sun Prairie, Wis.

[21] Appl. No.: 661,251

[22] Filed: Feb. 25, 1976

[51] Int. Cl.$^2$ .............................................. A61B 17/12
[52] U.S. Cl. ...................................... 128/325; 128/339; 128/346; 128/DIG. 21
[58] Field of Search ............... 128/326, 325, 327, 335, 128/335.5, 334 C, 334 R, DIG. 21, 339, 346; 138/91, 89, 118; 24/115 H, 115 G, 136 R, 260

[56] References Cited

U.S. PATENT DOCUMENTS

| 269,468 | 12/1882 | Rounds | 24/260 X |
| 1,044,302 | 11/1912 | Underhill | 24/115 G X |
| 1,689,889 | 10/1928 | Nunes | 24/260 |
| 2,581,114 | 1/1952 | Larson | 128/327 X |
| 2,928,395 | 3/1960 | Forbes et al. | 128/335.5 |
| 2,936,759 | 5/1960 | Yuhas | 128/171 X |
| 3,735,765 | 5/1973 | Ichelson | 128/346 X |
| 3,762,418 | 10/1973 | Wasson | 128/326 X |
| 3,875,946 | 4/1975 | Duncan | 128/339 |
| 3,880,166 | 4/1975 | Fogarty | 128/325 |
| 3,892,240 | 7/1975 | Park | 128/339 |
| 3,910,280 | 10/1975 | Talonn | 128/327 |
| 3,914,801 | 10/1975 | Dick et al. | 128/335.5 X |
| 3,993,076 | 11/1976 | Fogarty | 128/325 |

FOREIGN PATENT DOCUMENTS

| 116403 | 1/1943 | Australia | 128/327 |

Primary Examiner—Robert W. Michell
Assistant Examiner—Michael H. Thaler
Attorney, Agent, or Firm—Theodore J. Long; Harry C. Engstrom; Nicholas J. Seay

[57] ABSTRACT

A surgical tape in one embodiment having an elastomeric tubular body with the ends of the tubular body sealed to entrap air therein at substantially atmospheric pressure. A curved metal needle may be affixed to one end of the tubular body to facilitate insertion of the tape device between body structures. A clamping pad may be attached to the tubular body at a point intermediate the ends thereof. The clamping pad is adapted for use in ligating blood vessels by engaging the blood vessel between the clamping pad and a portion of the tubular body and drawing the tubular body into engagement with a jaw portion of the clamping pad.

9 Claims, 10 Drawing Figures

SURGICAL TAPE DEVICE

BACKGROUND OF THE INVENTION

1. Field of the Invention

This invention pertains generally to the field of surgical appliances and instruments, and more particularly to surgical tape utilized to restrain, hold, or partially or fully ligate body structures.

2. Description of the Prior Art

It is commonly necessary during surgical procedures to manipulate organs and other structures within the operating area, and to hold these structures away from the area where the surgeon is working. This necessary restraint and manipulation of body organs and structures is often accomplished by passing a string-like material under the organ and pulling on the string to hold back the organ. It is apparent that such procedures must be accomplished with minimal trauma to the body organs being manipulated.

It is also a common surgical procedure to ligate tubular body structures such as blood vessels and organ ducts to prevent flow therethrough during the surgical procedures. Such ligations are commonly accomplished by applying tension to the vessel with a non-elastic suture material where the use of a hemostat is not necessary or desirable. Such tension and pulling on body structures by non-elastic materials and the like is often accompanied by damage to the rather fragile tissue structures. Substantially flat solid elastic tapes have been used in place of the non-elastic tapes, but if such tapes are twisted or not oriented properly; they may tend to dig into body tissues. Hollow open elastic tapes have also been utilized, but such hollow tapes will not easily roll when pulled along body structures and may twist in use, thereby presenting the possibility of injury to delicate body tissues.

SUMMARY OF THE INVENTION

I have invented a surgical tape device which can be utilized to ligate or apply pressure to blood vessels, organ ducts or other body structures with minimal trauma to the body tissues involved. My surgical tape device has an elongated tubular body composed of an elastomeric material which is preferably silicone elastomer. The elastomeric quality of the tubular body provides the highly desirable advantage of allowing the tubular body to yield when in contact with body tissues, thus controlling the amount of pressure that is applied to the tissues or the pressure by which body structures such as blood vessels and organ ducts are shut off.

The hollow tube provides a lumen therein which enhances the elastic qualities of my tape and provides for greater "give" when the tape is in contact with the body structure. The ends of the tubular body of my invention may be sealed with sealing means such as silicone elastomer which is preferably applied in a liquid state thereto within the lumen, and which is self curing to a solid state adhering to the walls of the lumen. Because the ends of the tape are sealed to entrap air at substantially atmospheric pressure within the lumen, my surgical tape will resist collapsing when in contact with a body structure, a common and undesirable occurence with ordinary hollow elastic tubing. The collapsing of ordinary hollow tape brings the interior wall of the tape into rubbing contact with itself, allowing such tape to easily twist and inhibiting rolling of the tape when pulled along a blood vessel or the like. The sealed tubular body of my invention prevents the inside surface of the lumen from easily coming into contact with itself and greatly reduces twisting of the tape. When the sealed tubular body is compressed by a surgical instrument or by hand, the pressure in the lumen is actually increased above atmospheric pressure, which inhibits collapsing of the tubular body and facilitates rolling of the body along a blood vessel. For convenience, the ends of the tape may be color coded by coating them with an elastomeric material compatible with that of which the tubular body is composed, and which has a selected color impregnated therein.

In a modification of the surgical tape device of my invention, a needle without a cutting edge is affixed to one of the sealed ends of the tubular body, with a portion of the end of the tubular body extending into the hollow interior of the metal needle, which is preferably curved. The tubular body is sealed and affixed to the interior of the needle, with no obstructions being present on the exterior of the needle or of the tubular body which could interfere with passage of the needle and tubular body through various body tissues.

A further embodiment of my surgical tape device employs a clamping pad attached to the tubular body at a point intermediate the ends thereof. The clamping pad is attached at one end thereof to the tubular body and has a jaw portion at the other end thereof. A blood vessel or organ duct may be easily and quickly ligated with a desired amount of pressure by simply holding the blood vessel between the clamping pad and one of the free portions of the tubular body portion, drawing the tubular body over the blood vessel so as to hold the blood vessel between the tubular body and the pad, and then drawing the tubular body into the jaws of the clamping pad to securely and releasably hold it therein. The amount of pressure applied to the blood vessel can be adjusted by pulling the tubular body through the jaws of the clamping pad to a greater or lesser degree. The pressure on the blood vessel can thus be controlled, as desired, to prevent any blood from passing through the vessel or to close the blood vessel only partially. The clamping pad can thus be utilized in such applications as arterial catheterization to prevent flow of blood but to allow a catheter to be passed up an artery which has pressure applied to it by the clamping pad and tubular body.

Further objects, features and advantages of my invention will be apparent from the following detailed description taken in conjunction with the accompanying drawings showing preferred embodiments of a surgical tape device exemplifying the principles of my invention.

DESCRIPTION OF THE PREFERRED EMBODIMENTS

Figure 1:
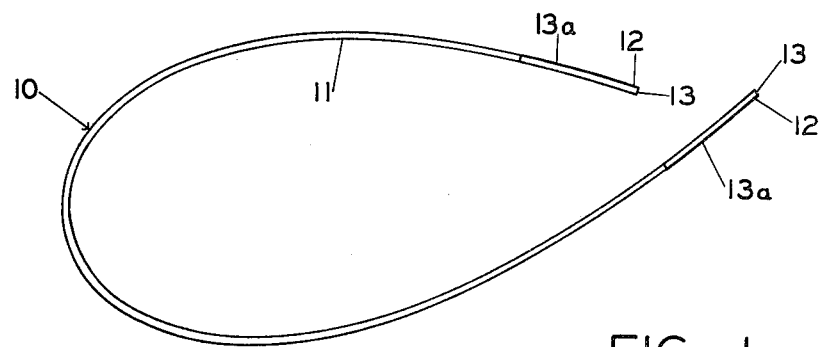
FIG. 1 is an exterior view of my surgical tape device.
Figure 2:
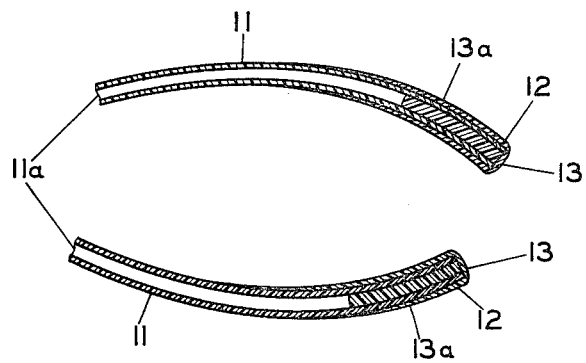
FIG. 2 is a broken enlarged cross sectional view of the surgical tape device of FIG. 1.

Referring now more particularly to the drawings, wherein like numerals refer to like parts throughout the several views, a preferred embodiment of a surgical tape device in accordance with my invention is shown generally at 10 in FIG. 1. The surgical tape 10 has a tubular body 11 which is composed of an elastomeric material, preferably silicone elastomer because of the compatibility of this material with body tissue. Various radiopaque substances such as barium compounds may be added to the elastomer so that the tape 10 will be visible on X-ray pictures. As best shown in the cross sectional view in FIG. 2, the tubular body 11 has a substantially open lumen 11a which is unobstructed between the two ends 12 of the tubular body and which has air at substantially normal atmospheric pressure therein. The ends 12 of the tubular body are sealed with a fluid-tight seal 13 to prevent the air within the lumen 11a from escaping, with the sealing preferably being accomplished by filling the lumen 11a for a small distance from the ends 12 with a solid elastomeric material such as the elastomer of which the tubular body itself is composed. A preferred manner of sealing the ends of a tubular body composed of silicone elastomer is to slightly compress a portion of the tubular body, dip the ends of the tubular body in liquid silicone elastomer, and release the tubular body to allow silicone elastomer to be drawn into the lumen 11a, with the silicone hardening and adhering to the tubular body upon curing, with the liquid silicone used preferably being of the type which self cures by reacting with moisture in the air. It is also desirable to color code the various tapes to allow the surgeon to distinguish between the tapes he is using and thus the solid material which seals the lumen 11a of the tape may also be provided as a coating 13a to a portion of the exterior of the tubular body at the ends thereof as shown in FIG. 2, and this coating may be colored with a selected coloring material.

Figure 3:
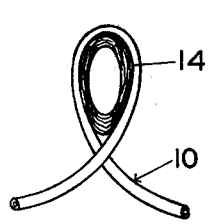
FIG. 3 is a view of a portion of the surgical tape device of FIG. 1 in position to close off a blood vessel shown in cross section.

Because the ends 12 of the air cushion tape 10 are sealed, the tape will resist twisting when it is pulled around an artery, vein or other body structure and will tend to roll along such body vessels. As best shown in FIG. 3, the air cushion tape 10 will tend to fully engage a blood vessel 14 as the tape is drawn tight, but will resist collapsing such that the inner surface of the lumen 11a would come into contact and rub against itself. The air cushion within the lumen is actually enhanced when the tubular body is compressed by surgical instruments or by hand, since such compression increases the air pressure inside the lumen above atmospheric pressure. Because the air cushion within the lumen of the tape 10 inhibits the opposite sides of the inner surface of the lumen 11a from coming into contact with each other, the tape 10 can roll along a blood vessel, thereby minimizing a major source of trauma to the blood vessel associated with ordinary flat tapes or nonair cushioned elastic tapes.

It is preferred that the diameter of the interior lumen 11a be a substantial portion of the diameter of the tubular body 11 to allow the tubular body to compress and stretch easily when in contact with delicate body structures. A lumen diameter approximately one half or more of the tubular body outside diameter provides preferred qualities of compressibility and stretch. Because the air cushion tape is utilized with relatively small body structures, the maximum useful outside diameter of the tubular body would be in the range of 150 thousandths of an inch, with such large tape devices being used for ligating only the largest arteries. Larger diameter devices are not desirable since the relatively small body structures could not be fully engaged, and the danger of the tubular body folding and pinching a blood vessel is increased.

Figure 4:
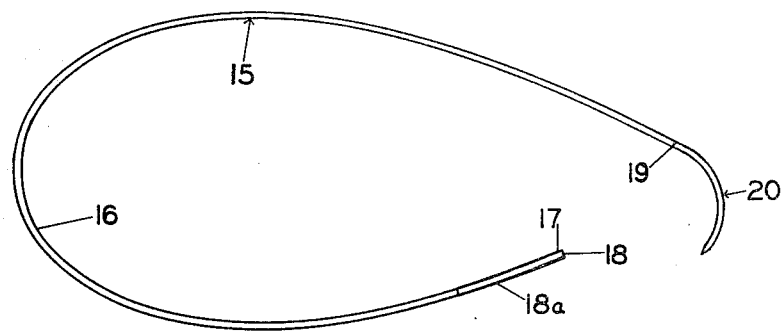
FIG. 4 is an exterior view of another embodiment of my surgical tape device having a curved needle end portion.

Another embodiment of my surgical tape device is shown generally at 15 in FIG. 4. The tape device 15 has a tubular body portion 16 having an interior lumen 16a, which is comprised of an elastomeric material, preferably a silicone elastomer. The preferred dimensions of the tubular body 16 are the same as described above for the tubular body 11 of the surgical tape 10. One end 17 of the surgical tape device 15 has a fluid tight seal 18 of elastomeric material formed in the manner described above for the air cushion tape 10. The sealing material of the seal 18 which is applied to the end of the tape may also be applied as a coating 18a to the exterior of the tape, as shown in FIG. 4, with a coloring material added thereto to allow color coding of the tape. The other end 19 of the tape 15 has a needle portion 20 affixed thereto.

Figure 5:
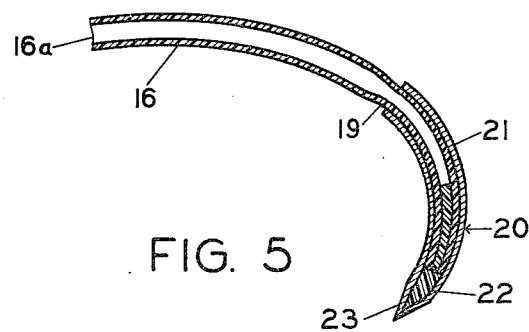
FIG. 5 is an enlarged cross sectional view of the surgical tape device of FIG. 4 showing the needle and the attachment of the tubular body portion to the needle.

The needle portion 20 and its attachment to the body 16 of the tape device 15 is best shown in the cross sectional view of FIG. 5. The needle 20 has a hollow tube portion 21 into which the end portion of the tubular body 16 extends. As shown in FIG. 5, the interior of the lumen of the tube portion 21 is preferably of smaller diameter than the exterior diameter of the elastomeric tubular body 16, thus requiring that the tubular body 16 be compressed within the hollow tube portion 21. An air cushion at substantially atmospheric pressure is provided within the tape 15 by providing a fluid tight seal 22 at the end 19 which is composed of a sealing material such as silicone elastomer. The seal 22 of silicone elastomer may be applied to the end of the tape 15 in a liquid state, with the elastomer curing to a solid state in a manner similar to that described above for the surgical tape device 10. The needle 20 has a pointed end 23 which is provided to enable the needle to be passed through soft body material or between separate adjacent body tissues. It is preferred that the needle 20 not have a cutting edge so as to reduce the possibility of inadvertently puncturing or penetrating body tissues. The curved needle 20 shown in FIG. 5 is preferably formed from a straight piece of hollow metal tubing such as stainless steel tubing, with the elastomeric tubular body portion 16 being drawn into the hollow interior of the tubing. The end 19 of the elastomeric tubular body then has the seal 22 formed thereon by application of the liquid sealing material as described above. As best shown in FIG. 5, the seal 22 should extend within the tubular body 16 such that when the hollow metal tubing is curved as described below, the silicone elastomer seal 22 within the tubular body portion 16 will also be curved to affix the tubular body within the hollow needle. The free end of the straight metal tube is then swaged to form the point 23. This construction is preferred since it provides an unobstructed connection of the needle to the tubular body, and a smooth needle with an unobstructed exterior. The needle is preferably curved as is customary with surgical needles. The curved needle 20 allows the surgical tape device 15 to be pulled around organs and through tight spaces which would otherwise be difficult to reach, while the air entrapped in the interior lumen 16a of the tubular body inhibits the tape from folding or twisting, and thereby tends to prevent injury to blood vessels, ducts or other body structures around which it is pulled or engaged for ligation.

Figure 6:
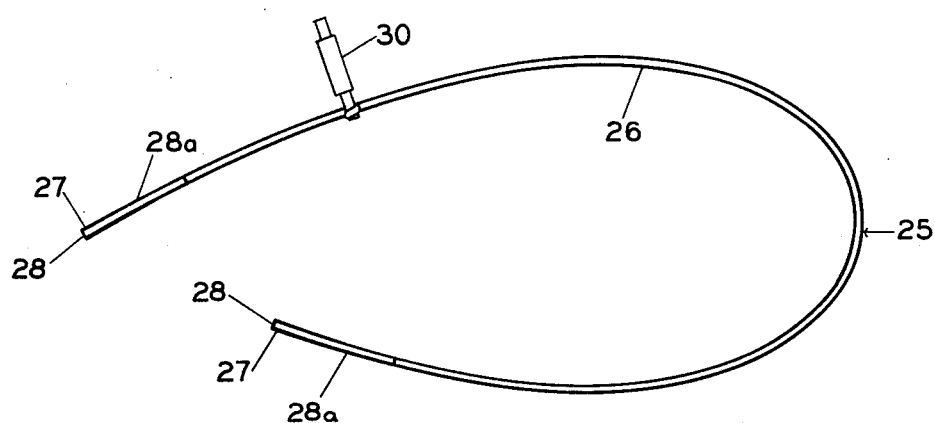
FIG. 6 is an exterior view of another embodiment of my surgical tape device having a clamping pad.

A further embodiment of a surgical tape device especially adapted for temporarily and quickly ligating blood vessels is shown generally at 25 in FIG. 6. The surgical tape device 25 has a tubular body 26 made of an elastomeric material such as silicone elastomer, and is preferably plugged and sealed at each of the two ends 27 thereof with a seal 28 in a manner similar to that described above for the air cushion tape 10 to entrap air at substantially atmospheric pressure therein, although the surgical tape device 25 may satisfactorily employ a non-air cushioned hollow elongate elastomeric body or a solid elongate elastomeric body for some applications. The sealing of the ends 27 is preferred since this construction provides the same air cushioning advantages for the tape device 25 as are described above for the tape device 10. A colored elastomeric coating 28a may be applied to a portion of the exterior of the tubular body 26 at the ends thereof to provide color coding. The surgical tape device 25 has a clamping pad 30 attached to the tubular body at a point intermediate the ends thereof. A blood vessel or other duct may be quickly and releasably closed or partially occluded between the tubular body 26 and the pad 30, as described more fully below.

Figure 7:
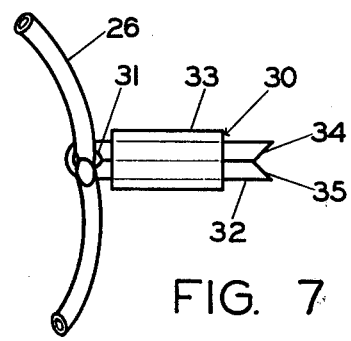
FIG. 7 is another view of a portion of the surgical tape device of FIG. 6 showing the clamping pad.

The attachment of the tubular body portion 26 to the pad 30 is best shown in FIG. 7. As shown therein, the tubular body 26 is preferably passed up through an opening 31 in a clamping jaw portion 32 of the pad 30 and may be wound around the outside of the pad and back through the opening 31 to prevent the pad 30 from sliding along the tubular body 26. The pad may alternatively be glued or otherwise affixed to the tubular body as desired.

A sleeve 33 is fitted tightly over the clamping jaw 32. The clamping jaw is preferably made of a stiff but resilient plastic material, whereas the sleeve 33 is preferably made of a softer elastomeric material, and may be transparent as illustrated in FIG. 7. The clamping jaw portion 32 and the sleeve portion 33 are shown in disassembled relation in FIG. 8. The clamping jaw portion 32 has a substantially straight first jaw member 34 and a similar second jaw member 35 attached together by a thinner and more easily bendable resilient hinge portion 36 formed integrally with the jaw members.

Figure 8:
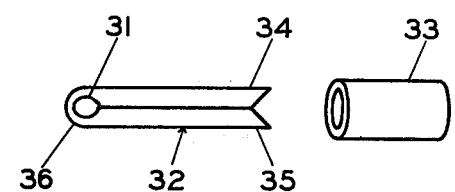
FIG. 8 is an exploded view of the clamping pad portion of the surgical tape device of FIG. 6 showing the relation between the jaw portion and the tubular sleeve portion of the clamping pad.
Figure 9:
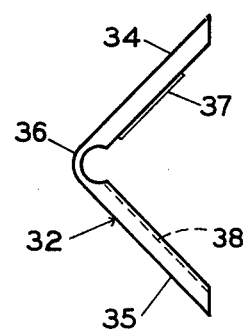
FIG. 9 is a detailed view of the jaw portion of the clamping pad of the surgical tape device of FIG. 6 in open disassembled position.

The clamping jaw 32 is preferably composed of a stiff but resilient material such as nylon or polyethylene which will bend slightly to allow the tubular body portion to slip between the jaw members 34 and 35. As best shown in FIG. 7, the sleeve 33 does not cover the entire length of the clamping jaw, but leaves uncovered the end of the clamping jaw opposite the end at which it is attached to the tubular body so that the tubular body may be engaged with and restrained between the jaw members 34 and 35. The ends of the jaw members 34 and 35 are preferably beveled as shown to assist in guiding the tubular body so that it may be more easily inserted between the jaw members and releasably held therebetween. The preferred construction of the clamping jaw is shown in FIG. 9, wherein the clamping jaw is in an opened position. An integrally formed ridge 37 extends along the inner edge of the first jaw member 34 for part of the length of the first jaw member, with this ridge 37 fitting into a mating groove 38 on the inner side of the second jaw member 35. The interaction of the ridge 37 with the groove on the inner surface of the second jaw member, when the clamping jaw is in its closed position as shown in FIG. 8, prevents the jaw members 34 and 35 from laterally slipping in relation to one another.

The sleeve 33 preferably consists of a hollow tube-like structure of resilient material which has an inside lumen having a diameter somewhat less than the outside dimensions of the clamping jaw when it is in its closed position. The sleeve 33 must be expanded to allow it to slip over the clamping jaw 32, and thus the resilient sleeve tends to hold the clamping jaw 32 in its closed position with the jaw members 34 and 35 in engagement.

Figure 10:
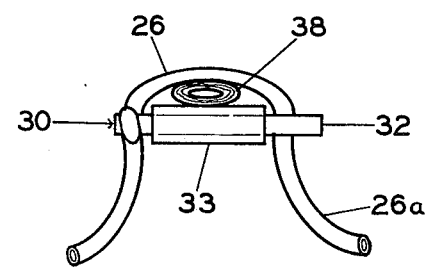
FIG. 10 is a view of the surgical tape device of FIG. 6 in position to ligate a blood vessel shown in cross section.

The use of the surgical tape device 25 with clamping pad 30 is best illustrated with reference to FIG. 10, which shows the device partially ligating a blood vessel 38 which is shown in cross section. The surgeon places the sleeve 33 of the pad 30 against the vessel 38 which is to be occluded, and then draws the tubular body 26 of the surgical tape device around the blood vessel. The tubular body is brought into contact with the jaw portion 32 and is pulled into and between the jaw members 34 and 35 so that the jaw portion will firmly engage and releasably hold the tubular body. The extent to which the blood vessel 38 is closed off is determined by the amount of pressure applied between the tubular body 26 and the sleeve 33 of the pad. This pressure may be increased by drawing the elastic tubular body 26 more tightly across the vessel 38 and pulling it between the jaw members 34 and 35 to hold it therebetween at a greater tension. The surgeon may easily release the blood vessel 38 from its closure between the tubular body 26 and the pad 33 by pulling outwardly on the free portion 26a of the tubular body to pull it out of engagement with the jaw portion 32 and thus release the pressure on the blood vessel. Because the tubular body 26 is formed of an elastomeric material, the pressure on the vessel 38 can be controlled, since high pressures within an artery, for example, will expand the artery under the force of the elastomeric tubular body 26 and allow some blood to pass therethrough. Furthermore, a catheter may be passed through an artery closed off by the tape devices to blood flow, but which can expand under further pressure to allow the catheter to pass. With the use of an air cushioned tubular body 25, the possibility of the tubular body twisting or folding against the blood vessel, with resulting injury to the vessel, is minimized.

It is understood that my invention is not confined to the particular construction and arrangement of parts herein illustrated and described, but embraces all such modified forms thereof as may come within the scope of the following claims.

I claim:

1. A surgical tape device, comprising:

(a) an elongated tubular body composed of a silicone elastomeric material having a lumen therein and an exterior diameter of less than about 150 thousandths of an inch, and having two ends;

(b) a fluid-tight seal of silicone elastomeric material filling each of the ends of said tubular body to entrap air within said lumen at substantially atmospheric pressure;

(c) a hollow curved needle having an interior of smaller diameter than the normal exterior diameter of said tubular body, said hollow curved needle being securely attached to said tubular body at one end thereof by engagement of the end of said tubular body within a substantial length of a curved portion of the hollow interior of said needle whereby the elastomeric seal which fills the end of the tubular body is curved by conformity of the tubular body to the curved portion of the needle to affix the tubular body within the needle, said needle having a point formed on the end thereof.

2. The surgical tape device as specified in claim 1 including a coating of silicone elastomeric material on a portion of the exterior of said tubular body at the end thereof which is opposite to the end having said needle affixed thereon, said elastomeric material being of a selected color to thereby provide color coding of the surgical tape device.

3. A surgical tape device, comprising:

(a) an elongated body composed of an elastomeric material and having two ends; and (b) a clamping pad attached to said elongated body at a point intermediate the ends thereof, said clamping pad having a jaw portion and an elongated elastomeric sleeve which fits over and resiliently holds said jaw portion, said jaw portion being formed of stiff but resilient material having first and second jaw members attached together by a resilient hinge portion formed integrally therewith, said sleeve member fitting over and restrainably holding said first and second jaw members in engagement over a portion of the length of said jaw members, a portion of the length of said jaw members being unobstructed to allow insertion of said elongated body between said first and second jaw members to restrainably engage and releasably hold said elongated body, whereby a body vessel may be emplaced between said elastomeric sleeve and a portion of said elongated body intermediate the point of its attachment to said clamping pad and the point of its engagement between said jaw members to apply pressure to said body vessel which may be adjusted by the position at which said elongated body is drawn into said jaw members of said pad.

4. The surgical tape device as specified in claim 3 wherein said elongated body is tubular and has a lumen therein, and including a fluid-tight seal of elastomeric material filling each end of said elongated tubular body to entrap air within said lumen at substantially atmospheric pressure.

5. The surgical tape device as specified in claim 4 wherein said elongated body and fluid-tight seal are composed of silicone elastomer.

6. The surgical tape device as specified in claim 3 including a coating of elastomeric material on a portion of the exterior of said elongated body at the ends thereof, said elastomeric material being of a selected color to thereby provide color coding of the surgical tape device.

7. The surgical tape device as specified in claim 3 including a hollow tubular curved metal needle affixed to said elongated body at one end thereof, said one end of said elongated body extending into the hollow interior of said needle, said needle having a point formed on the end thereof.

8. The surgical tape device as specified in claim 3 wherein the outside diameter of said elongated body is less than 150 thousandths of an inch.

9. The surgical tape device specified in claim 3 wherein said first jaw member has a longitudinal ridge extending along the surface thereof which engages said second jaw member, and wherein said second jaw member has a groove which receives said longitudinal ridge in mating relation when said jaws are in engagement to prevent lateral slipping of the jaw members with respect to one another.

* * * * *